US00PP14319P39

(12) United States Plant Patent
Moon

(10) Patent No.: US PP14,319 P3
(45) Date of Patent: Nov. 25, 2003

(54) DEODAR CEDAR NAMED 'CDMTF2'

(50) Latin Name: *Cedrus deodara sp.*
Varietal Denomination: CDMTF2

(75) Inventor: Dwayne C. Moon, Loganville, GA (US)

(73) Assignee: Tree Introductions, Inc., Bishop, GA (US)

( * ) Notice: Subject to any disclaimer, the term of this patent is extended or adjusted under 35 U.S.C. 154(b) by 1 day.

(21) Appl. No.: 09/855,291

(22) Filed: May 14, 2001

(65) Prior Publication Data

US 2002/0170098 P1 Nov. 14, 2002

(51) Int. Cl.[7] ..... A01H 7/00

(52) U.S. Cl. ..... Plt./213

(58) Field of Search ..... Plt./213

(56) References Cited

U.S. PATENT DOCUMENTS

PP11,979 P2 * 7/2001 Moon ..... Plt./213

* cited by examiner

*Primary Examiner*—Bruce R. Campell
*Assistant Examiner*—W C Haas
(74) *Attorney, Agent, or Firm*—Klarquist Sparkman LLP

(57) ABSTRACT

A Deodar Cedar tree named 'CDMTF2' having a rapid growth rate, dense branching and a large root system and which also is capable of being reproduced reliably using vegetative cuttings.

3 Drawing Sheets

Latin name of genus and species: *Cedrus Deodara* 'CDMTF2'.

DESCRIPTION

The present invention relates to a new and distinct variety of *Cedrus deodara*, Deodar Cedar, which has been given the varietal name 'CDMTF2'.

I discovered my new tree in spring 1993 as a chance seedling (parentage unknown) of Deodar Cedar growing in a cultivated area of a nursery in Walton County, Ga. The original tree grew from a seed planted in spring 1991. The seedling was purchased as a 12–18" liner as part of a group of 500 liner tree in spring 1992. In the spring of 1993, it became apparent to me that this new tree was larger and had a superior root system. This was based on a comparison with about one hundred and fifty trees that were selected from the group of 500 liner trees based on size, shape, root development and overall uniformity.

This new tree had a superior growth rate compared to the other trees of this group. After six growing seasons, this new tree was 16 feet in height, full, and uniform. Two other trees of this group were 14 feet in height, and the remaining trees were 10 feet or less in height. In the spring of 1999, my new tree was transplanted to an observation site in Oconee County, Ga. where it has remained since that time. It is now 10 years old from a seed.

As I observed the original tree of my new variety, the uniqueness of this tree became apparent because of its rapid growth rate, dense branching and superior root system compared to other Deodar Cedar cultivars known to me. This combination of characteristics distinguish my new tree from other Deodar Cedars known to me.

In 1998 this tree was successfully propagated by vegetative cuttings at my direction at a nursery in Georgia, and the progeny have proven to retain the dense branching and rapid growth rate and superior root of the original tree, and thus reproduce true to type.

I observed this new tree variety for a period of time and believe it is particularly useful as a specimen evergreen and is suitable for large areas such as parks or other natural areas. Like other Deodar Cedar cultivars, my new variety is also suitable for planting as screen for windbreaks or as a control for noise pollution. My new tree has the added benefit of a fast growth rate and superior root system. These latter two attributes will improve the transplant success and livability of the trees in a landscape. My new tree will also provide the clonal consistency needed in planned landscapes.

Cultivated Deodar Cedar is largely represented in the industry by seedling material, although there are approximately fifty different recognized forms and cultivars. Seedling Deodar Cedar is widely variable in growth habit, but typically display the graceful pendulous branching that typifies the species. My new variety has less pendulous branching than most clones and some seedlings.

Many clones, such as 'Kashmir' (unpatented), 'Kingsville,' (unpatented) and 'Shalimar,' (unpatented) are selected for cold hardiness while others such as 'Eisregen' (unpatented) and 'Karl Fuchs' (unpatented), have also been selected for their bluish needle color. Yellow needled and yellow variegated forms such as 'Aurea' (unpatented) and 'Golden Horizon' (unpatented) have also been selected, and there is at least one white variegated form named 'Albospica.' (unpatented) There are also several dwarf forms, both variegated and non-variegated, including 'Compacta' (unpatented), 'Blue Dwarf,' (unpatented) 'Emerald Spreader,' (unpatented) and 'Pygmy.' (unpatented) Several forms have been selected for their weeping nature, namely 'Pendula.' (unpatented) There are a few cultivars that have dense or upright habits. 'Descanso Dwarf' (unpatented) is an upright and compact plant that also has bright green foliage and semi-pendulous branching. 'Deep Cove' (unpatented) is an upright growing, pyramidal shaped tree with dense foliage that emerges a stark white. 'Blue Snake' (unpatented) is an extremely upright plant with sparse, weeping branches. It is notable that cultivars described as dense are also slower growing and typically more shrub-like in habit. The tree forms of typical Deodar Cedars are usually less dense and more wide-spreading.

Insofar as known by the inventor, 'Blue Dwarf', 'Decanso Dwarf' and 'Deep Cove' and the other varieties mentioned above are not patented.

My new tree has exhibits a rapid growth rate, dense branches and has a superior root system not represented by seedlings known to me or any other cultivar known to me.

Typical Deodar Cedar varieties are broadly pyramidal in youth with pendulous branches, becoming wide-spreading and flat-topped with age. My new tree has this broad pyramidal shape now, and is expected to become more wide-spreading with age. My new tree has an overall form typical of most seedlings and some selected Deodar Cedars, with spreading branches and a bluish needle color. In form, my new tree compares to 'Aurea', 'Eisregen', 'Gold Cone' (unpatented) and 'Karl Fuchs.' However, my new form has less pendulous branching than all four of these selections and is bluer in needle color than all except 'Karl Fuchs'. Compared to 'Karl Fuchs', my new variety holds its branches more laterally and has a less blue needle color. My new tree has needle color similar to 'Blue Snake' (unpatented), but my new tree has a broader, fuller form with less pendulous branching than 'Blue Snake'. To my knowledge, my new tree has a rapid growth rate and superior root system that is not represented by any other known Deodar Cedar cultivar or seedling. Compared to the group of five hundred seedlings it was selected from, my new tree grew about 50% faster than 98% of the group, and compared to the selection 'Kashmir' growing on a similar site in Northeast Georgia, my new tree is twice as fast. Typical Deodar Cedars reach 40 to 70' after 30 to 40 years, and can reach a height of 100' with equal spread. My new tree is expected to be at least this large.

My new variety has been asexually propagated by vegetative cuttings at my direction. This propagation and observation of the resulting progeny have proven the characteristics of my new variety to be firmly fixed and true to type.

The accompanying photographs depict the color of the tree and foliage of my new variety as nearly true as is reasonably possible to make the same in a color illustration of this character.

My 'CDMTF2' variety of Deodar Cedar is currently growing at a nursery, in Oconee County, Ga. Oconee County is in USDA Hardiness Zone 7, and the site has a clay-loam soil type and receives an average of 50 inches of rain each year. My new tree has not been lab tested for hardiness to compare it with any other cultivar, but my new tree has grown in USDA Zone 7 for about 10 years and has survived temperatures as low as 4 degrees F. in February 1996 with no apparent damage.

The original tree of my new variety, at about ten years of age, is currently about 6" in diameter at 12" above the ground. It is 20 feet high and 8 feet wide with a height to width ratio of 2.5. My new tree has not been observed under all growing conditions and thus variations may occur as a result of different growing conditions. Color often varies in a plant under certain growing conditions.

The following is a detailed description of my new variety of Deodar Cedar with color terminology in accordance with The Royal Horticultural Society (R.H.S.) color chart published by The Royal Horticultural Society of London. The observations are of the original tree growing at the observation site in Oconee, Ga.

Figure 1:
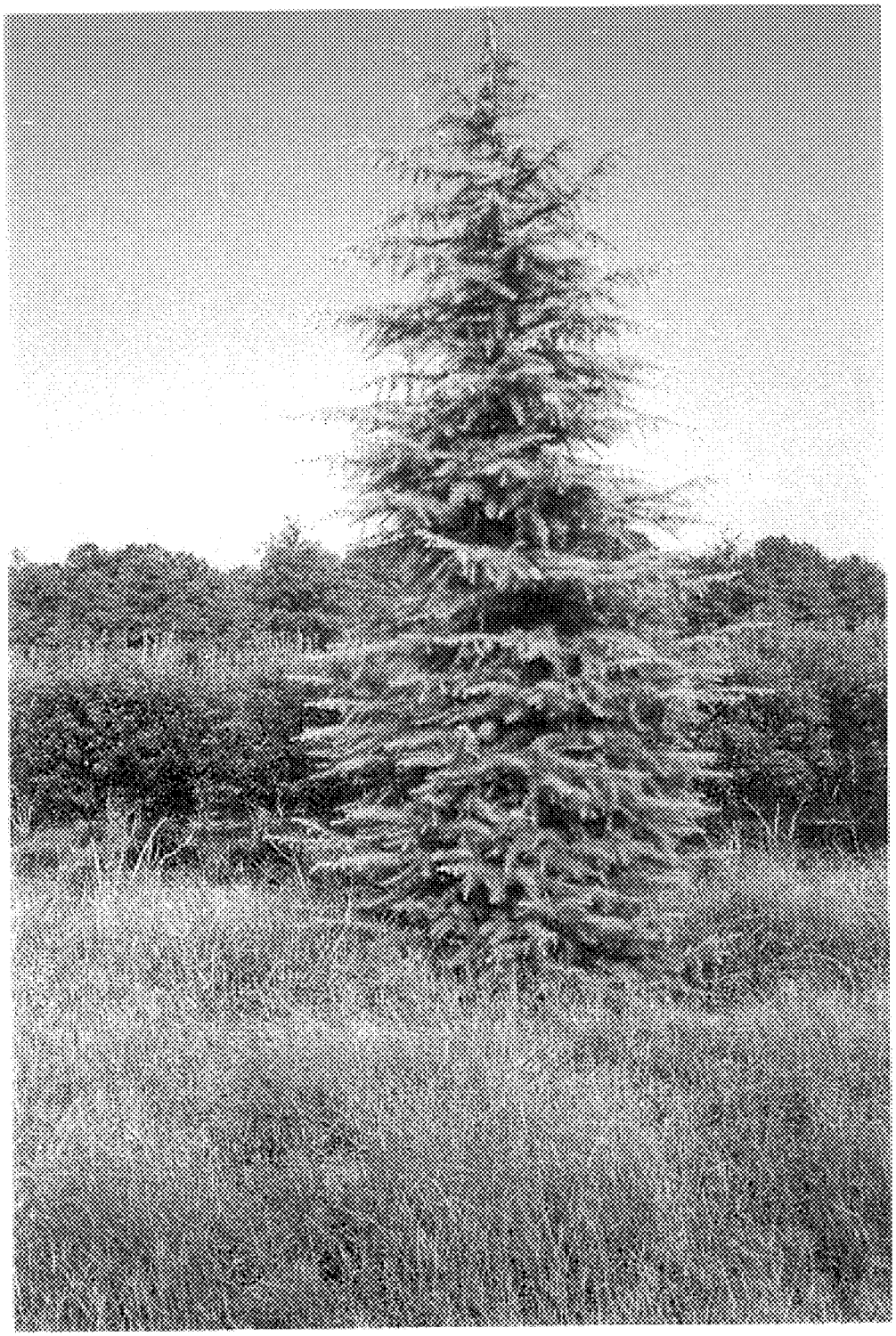
FIG. 1 is a photograph of an entire tree of my new variety.

Typical Deodar Cedar is broadly pyramidal in youth with pendulous branches, becoming wide-spreading and flat-topped with age. My new tree has this broad pyramidal shape now, and is expected to become more wide-spreading with age. My new tree has an overall shape typical of most seedlings and some selected Deodar Cedars, with spreading branches and a bluish needle color. The tips of the branches are slightly less pendulous than some of the cultivars and most seedlings known to me (FIG. 1).

To my knowledge, my new tree has a rapid growth rate and superior root system that is not represented by any other Deodar Cedar cultivar or seedling known to me. Compared to the group of five hundred seedlings from which it was selected, my new tree was 50% faster than 98% of the group. Compared to the selection 'Kashmir' growing on a similar site in Northeast Georgia, my new tree grew about twice as fast.

The trunk is typical of the species. Deodar Cedars have a strong central leader (bole). The bark color of my new tree is typical of the species. New stems are tan to grayish, maturing to a dark brown. Branching angles fall in the range typical of Deodar Cedar. The branching pattern and dendritic pattern is that of a single leader (bole). Branches at the top of the tree emerge at 15 degree angles to the main leader and tend to flatten with age. Branches at the base of the tree tend to be flatter, for example, at about a right angle to the main leader. Branches are uniformly and densely borne around the central leader with no large gaps from one branch insertion point to the next. As a result, my new tree is uniformly branched and symmetrical with a dense canopy (FIG. 1). In contrast, seedling Deodar Cedar and most of the cultivars known to me are usually more open. Also, the tips of the branches remain more erect than some of the cultivars and seedlings known to me.

Figure 2:
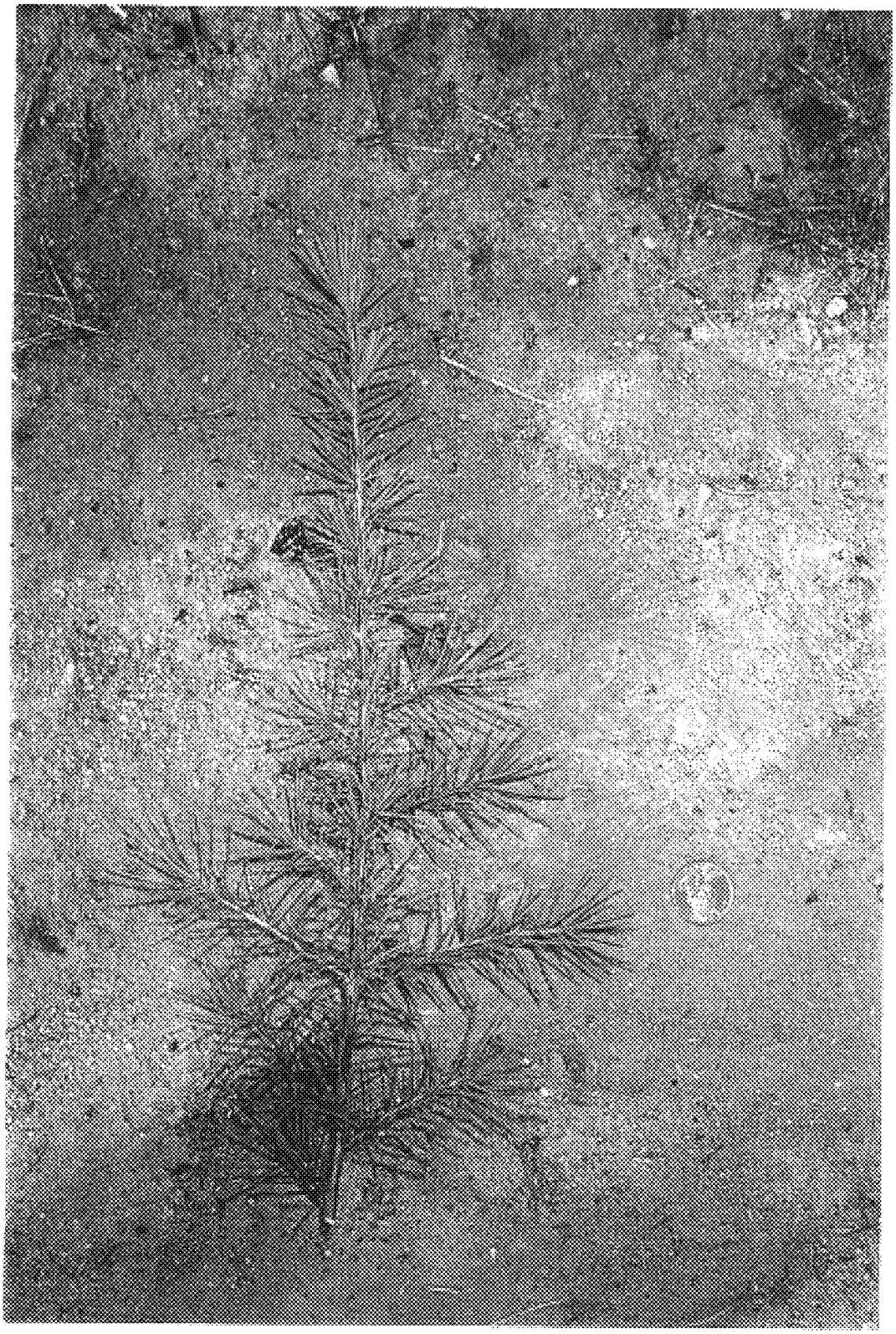
FIG. 2 is a close up of a branch showing the branching habit, needle color, and needle arrangement of my new variety.

Needles resemble the species but have a bluish hue (upper surface RHS 124B) not always seen in the species and found only in some cultivars. My new tree also tends to hold its needles one year longer than most Deodar Cedars, giving a fuller, denser appearance. In size the needles are typical of the species, 1 to 1½" long, borne in whorls of 15–20 positioned spirally along the branches (FIG. 2).

The buds are typical of the species. They are minute and ovoid with brown scales.

Figure 3:
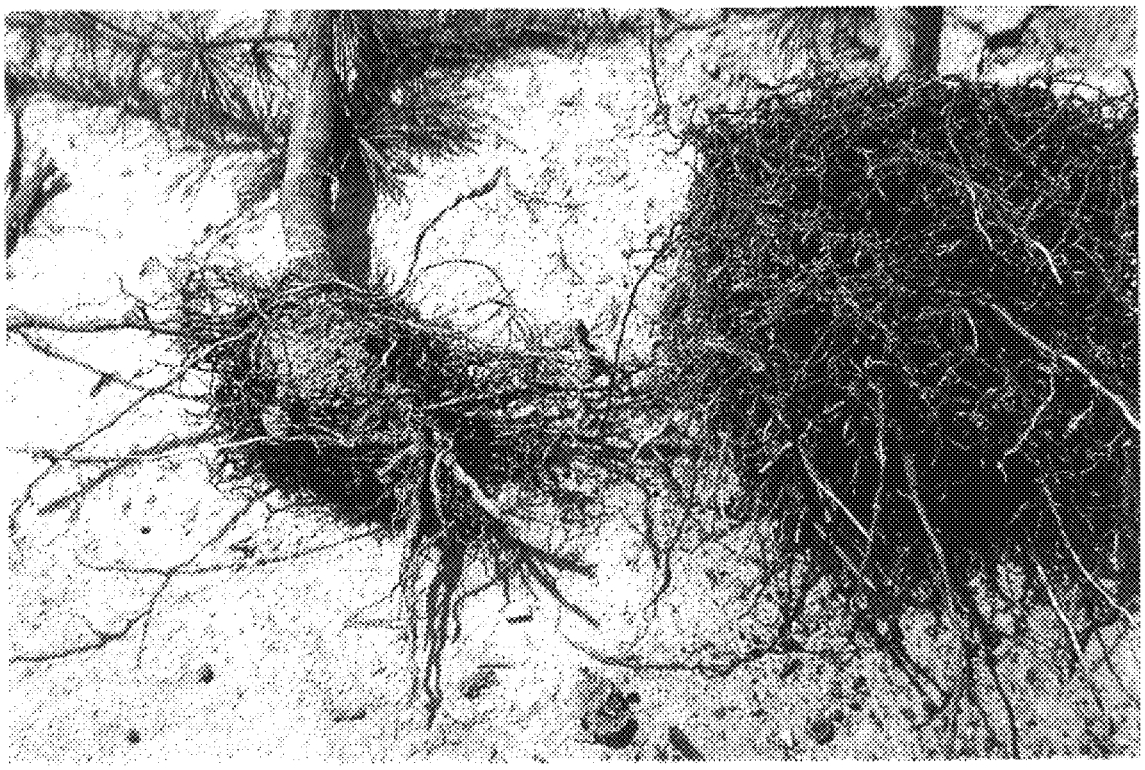
FIG. 3 is a close up of a typical seedling root system (on the left in FIG. 3) compared to a root system of a tree of my new variety (on the right in FIG. 3).

My new tree has not yet produced pollen, or produced cones. Whether the new variety is self fertile is not yet known. Deodar Cedar trees typically do not flower for up to 30 years The root system of my new tree is more fibrous than those of the species and other cultivars known to me (FIG. 3). Typical Deodar Cedar trees tend to have a root system of a medium density. When my new tree was transplanted from the liner field in 1993, its root system was noted as having approximately one-third more roots in comparison to other trees in the group. It is my belief that this fibrous root system contributes to the fast growth rate of the tree.

THE PLANT

Parentage: Initially discovered is a chance Deodar Cedar seedling of unknown parentage and was found growing in a cultivated area of a nursery in Walton County, Ga.

Tree shape: Broadly pyramidal. (FIG. 1). Ultimate height and width of the tree is unknown.

Trunk: The trunk is typical of the species with a strong central leader (bole). At about age ten, the initially discovered tree had a diameter of about six inches in diameter measured twelve inches above the ground.

Bark: The trunk bark color of my new tree is a brown color like RHS 197C, with dark brown speckles, like RHS 200C. New stems are yellow-green (RHS 146B) with grey-brown ridges (RHS 199C), maturing to a brown as shown by the trunk.

Branches: Branching angles fall within a range typical of Deodar Cedar. Branches at the top of tree emerge at about a 15 degree angle to the main leader and tend to flatten with age. Branches at the base of the tree tend to extend at about right angles to the main leader. Branches are uniformly and densely borne around the central leader with no large gaps form one branch emergence location to the next. A sampling of one year old branches from a group of typical trees of the variety growing in Oconee County, Ga. in 2002 had an average branch length of 20.5 inches, and an average branch diameter of 5/16 inch at the base and 1/8 inch at the tip.

Leaves: Size is typical of the species; 1 to 1½" long, borne in whorls of 15–20 spirally along the stems. Upper leaf surface color is a blue hue (upper leaf surface RHS 124B). Lower leaf surface is more green than upper leaf surface with not as much blue hue (lower leaf surface RHS 137C). (FIG. 2).

*Overall shape.*—Needle-like. Base: Pointed, less so than apex. Apex: Sharply pointed.

*Surface texture.*—Smooth, glaucous.

Buds: Buds are typical of the species; needles are minute and ovoid with brown scales.

Pollen and cones: My new tree has not yet produced pollen or cones.

Root system: The root system of my new tree is more fibrous than those of the species. (FIG. 3).

Pest and disease resistance: No unusual susceptibility to pests or disease has been observed.

Winter hardiness: No available information although the initially discovered tree has been exposed to winter temperatures which unofficially reached a low of about 40 degrees F.

I claim:

1. A new and distinct variety of Deodar Cedar tree substantially as herein shown and described, characterized particularly as to novelty by its rapid growth rate, dense branching and a large root system.

* * * * *